United States Patent [19]

Kurek

[11] 4,447,652
[45] May 8, 1984

[54] PREPARATION OF ALKYL ARYL ETHERS

[75] Inventor: Paul R. Kurek, Schaumburg, Ill.

[73] Assignee: UOP Inc., Des Plaines, Ill.

[21] Appl. No.: 380,808

[22] Filed: May 21, 1982

[51] Int. Cl.³ .............................................. C07C 41/06
[52] U.S. Cl. ..................................... 568/658; 568/630
[58] Field of Search ................................ 568/630, 658

[56] References Cited
U.S. PATENT DOCUMENTS 3,584,058 6/1971 Hahn .................................... 568/630
4,299,996 11/1981 Parlman .............................. 568/658

Primary Examiner—Bernard Helfin
Attorney, Agent, or Firm—James R. Hoatson, Jr.; Eugene I. Snyder; William H. Page, II

[57] ABSTRACT

Alkyl aryl ethers may be prepared in good yields by reacting a phenol with an olefin in the presence of an unmodified cationic exchange resin bearing sulfonic acid groups at low temperature. In another variation the ethers may be prepared by using as a catalyst the aforementioned resin where from about 10 to about 90 percent of the sulfonic acid groups are in the form of their alkali metal salts and the reaction temperature is greater than about 75° C.

5 Claims, No Drawings

PREPARATION OF ALKYL ARYL ETHERS

BACKGROUND OF THE INVENTION

Alkyl aryl ethers are excellent solvents for organic residues and are particularly good for dissolving the resinous or varnish-like deposits formed in the crankcase of internal combustion engines. They also are used as antioxidants, heat-transfer agents, and ingredients in perfumes. There seems to be no efficient and economical method of their preparation in commercial quantities. The Williamson synthesis appears to be the most important method and involves the reaction between an alkali metal salt of a hydroxy aromatic compound, that is, a phenol, and an alkyl halide or sulfate ester. Yields generally are low and there is a disposal problem for the alkali metal salt by-products.

Another approach to their preparation employs acid catalyzed addition of phenols to olefins. Generally this requires a strong acid and is conducted under heterogeneous conditions requiring separation of the acid. Where a solid phase catalyst is used, for example, aluminas and cationic exchange resins, the favored reaction usually is not O-alkylation to afford the alkyl aryl ethers, but is instead C-alkylation to afford ring-substituted phenols.

This precise problem was addressed by the patentee of U.S. Pat. No. 4,299,996 who observed that a fluorosulfonic acid resin was an effective catalyst for O-alkylation, whereas unmodified sulfonic acid resins themselves were not suitable for O-alkylation. Presumably this difference arose from the added acidity attributable to the strongly electron withdrawing fluorine atoms adjacent to the sulfonic acid group. Expressed differently, an influence from the aforementioned patent is that a particularly strong acidic resin is a prerequisite for its successful use as a catalyst in O-alkylation of phenols by olefins.

In view of the above, it was quite surprising to discover that ordinary cationic exchange resins may be successfully used as catalysts in the O-alkylation of phenols by olefins. An even more unexpected discovery is that when such resins are partially neutralized, that is, when they are partly in the form of their salts, they also are effective as O-alkylation catalysts, although under substantially different conditions than when used in the acid form.

SUMMARY OF THE INVENTION

Accordingly, an object of this invention is to prepare alkyl aryl ethers by alkylating phenols with olefins in the presence of a solid catalyst. In one embodiment the catalyst is an unmodified cationic exchange resin bearing sulfonic acid groups. In a more specific embodiment, said resin is a macroreticular resin. In yet another embodiment, the catalyst is a cationic exchange resin where from about 10 to about 90 percent of the sulfonic acid groups are in the form of a salt with an alkali metal.

DESCRIPTION OF THE INVENTION

The invention claimed herein is a method of preparing an alkyl aryl ether comprising contacting a phenol with an olefin in the presence of an unmodified cationic exchange resin bearing sulfonic acid groups at a temperature less than about 60° C. In a variant, the cationic exchange resin bears sulfonic acid groups of which from about 10 to about 90 percent are in the form of a salt of an alkali metal cation and the reaction temperature is greater than about 75° C.

In this specification a modified cationic exchange resin bearing sulfonic acid groups is one containing strongly electronegative atoms or groups in the resin backbone, thereby substantially increasing the acidity of the sulfonic acid groups borne by the resin. An example of such a modified resin is Nafion ®, a polyfluorinated product of E. I. DuPont. Conversely, an unmodified cationic exchange bearing sulfonic acid groups is one not containing such electronegative atoms or groups in the polymer backbone and whose acidity is typical of the sulfonic acid moiety.

This invention is based on the discovery, contrary to the prior art, that unmodified cationic exchange resins bearing sulfonic acid groups may be used successfully as a catalyst in O-alkylation of phenols under appropriate reaction conditions. An even more surprising observation leading to a variant of this invention is that when from 10 to about 90 percent of the sulfonic acid groups of such resins are converted to their alkali metal salts, the resulting material also is an effective catalyst for O-alkylation of phenols.

The phenols which may be used in the practice of this invention are hydroxy aromatic compounds generally, with mononuclear hydroxy aromatic compounds or phenols, being of greatest practical interest. The latter phenols are of the formula

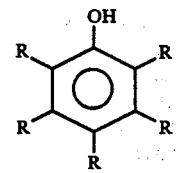

where each R may be hydrogen or an alkyl or cycloalkyl group, with those containing up to about 8 carbon atoms the most commonly employed. Examples of suitable groups include methyl, ethyl, propyl, butyl, pentyl, hexyl, heptyl, octyl, cyclopentyl, cyclohexyl, cyclopropyl, cyclobutyl, cycloheptyl, and cyclooctyl.

Examples of phenols which may be used in practice of this invention, cited solely for illustrative purposes, include methylphenyl (cresol), ethylphenol, propylphenol, butylphenol, pentylphenol, hexylphenol, heptylphenol, octylphenol, 2,3-dimethylphenol, 2,4-dimethylphenol, 2,5-dimethylphenol, 2,6-dimethylphenol, 3,4-dimethylphenol, 3,5-dimethylphenol, 2,3-diethylphenol, 2,3-dipropylphenol, 2,3-dibutylphenol, 2-methyl-3-ethylphenol, and so on; 2,4,6-trimethylphenol, 2,4,5-trimethylphenol, 2,3,5-trimethylphenol, 2,4-dimethyl-6-ethylphenol, and so forth.

The olefins which may be used in this invention contain from 3 to about 16 carbon atoms and have the general structure shown below.

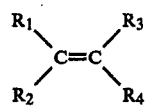

Each R group in the above structure is either an alkyl or hydrogen with from one to three R groups being alkyl. Examples of olefins, cited solely to illustrate this invention, include propylene, 1-butene, 2-butene, isobutylene, 1-pentene, 2-pentene, 2-methyl-1-butene, 3-methyl-1- butene, 2-methyl-2-butene, the isomeric hexenes, heptenes, octenes, nonenes, decenes, undecenes, dodecenes, tridecenes, tetradecenes, pentadecenes, and hexadecenes. Isobutylene is an especially preferred olefin in the practice of this invention.

In one aspect the catalyst of this invention is an unmodified cationic exchange resin bearing sulfonic acid groups. Both microreticular and macroreticular resins may be used but macroreticular resins are favored. When using the above catalysts the reaction temperature is less than about 60° C. with a temperature range from about 15° to about 25° C. preferred.

In another aspect of this invention the catalyst is an unmodified cationic exchange resin bearing sulfonic acid groups of which from about 10 to about 90 percent are in the form of their salt with an alkali metal cation. When such a catalyst is used a reaction temperature greater than about 75° C. is employed, with a temperature from about 80° to about 120° C. being preferred.

The O-alkylation performed according to this invention may be carried out either in a batch mode or in a continuous operation using, for example, a fixed bed, moving bed, fluidized bed, and so forth. Using a batch mode to illustrate this invention, for the case where the resin bears sulfonic acid groups, none of which are as salts, the phenol is mixed with about 1 molar proportion of olefin. Although excess olefin may be used it is quite desirable to have about equal molar proportions of olefins and phenols to minimize oligomer formation. The reactants are charged to a suitable vessel and the unmodified cationic exchange resin bearing sulfonic acid groups is then added.

The amount of resin is not critical, with from about 5 to about 10 wt.% resin, based on the phenolic reactant, being a generally convenient amount. The mixture is then stirred at a temperature less than about 60° C. with heat being removed, where necessary, by internal cooling. Reaction time will depend on the phenol and olefin used, the amount and exact nature of the resin, the temperature, and so forth, but generally will be in the range from about 1 to about 8 hours. When the reaction is complete the resin is removed by suitable means, as by filtration, and there is recovered the alkyl aryl ether produced in the reaction.

Where the catalyst is an unmodified cationic exchange resin bearing sulfonic acid groups of which from about 10 to about 90% are in the form of an alkali metal salt, the reaction is carried out substantially similar to the above description. However, a higher mole ratio of olefin may be used since oligomerization is not a major factor, with a mole ratio of 1 to about 8, more generally from about 1.5 to about 6, being commonly employed. The reaction is performed at a temperature above 75° C., preferably from about 80° to about 120° C.

The following examples are merely illustrative of this invention and are not intended to limit it in any way.

EXAMPLE I

To a 300 cc stainless steel autoclave was charged 86 g (0.8 mol) p-cresol, 45 g (0.8 mol) isobutylene, 10 g of Amberlyst® XN1010, which is a polystyrene-based, macroreticular sulfonic acid cationic exchange resin produced by Rohm and Haas. The pressure was adjusted to 100 psig with nitrogen and the mixture was stirred at 20° C. for 5 hours with the temperature being maintained by internal water cooling. The product was withdrawn, filtered to recover the catalyst, and analyzed by gas liquid phase chromatography. Its product composition was 28% p-cresol, 67% 4-methylphenyl t-butyl ether, and 5% 2-t-butyl-4 methylphenol. Thus, selectivity in ether formation was about 93%.

Another experiment was performed identically to that above except that the catalyst was IR-118®, a gel-type sulfonic acid cationic exchange resin produced by Rohm and Haas. Analysis showed 74% unreacted phenol, 25% 4-methylphenyl t-butyl ether, and 0.5% 2-t-butyl-4-methylphenol. Thus the ether was formed with even higher selectivity (98%) although the yield was less than that using a macroreticular resin.

EXAMPLE II

A mixture of p-cresol (0.4 moles), isobutylene (2 moles), and 10 g XN1010® about 80% of which was in the form of its sodium salt, was reacted at 100° C. for 3 hr. Analysis as described above showed 2.5% unreacted p-cresol, 18% mono- and 1.4% di-butylated methylphenol and 75% 4-methylphenyl t-butyl ether.

The following experiment was performed to show that the preceding results were not due to the 20% of the resin in its acid form. Conditions were identical to those described above except that 2 g XN1010® was used as the catalyst. Analysis showed no unreacted cresol, 44% 2-t-butyl-4-methylphenol, and 56% 2,6-di-t-butyl-4-methylphenol, a distribution quite different from that resulting above using partially neutralized resin. This comparison shows the partially neutralized resin gives results unique to itself as a species of catalyst.

What is claimed is:

1. A method of preparing an alkyl aryl ether comprising contacting a feedstock consisting essentially of a phenol of the formula,

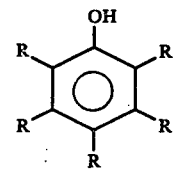

where each R is hydrogen or an alkyl group, and from about 1.5 to about 6 molar proportions of an olefin containing from 3 to about 16 carbon atoms of the formula,

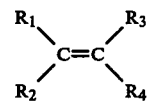

where each R is hydrogen or an alkyl group and from one to three such R groups are alkyl, with an unmodified macroreticular cationic exchange resin bearing sulfonic acid groups of which from about 10 to about 90 percent are in the form of their salt with an alkali metal cation at a temperature from about 80° C. to about 120° C., and recovering the alkyl aryl ether produced thereby.

2. The method of claim 1 where the phenol is phenol.

3. The method of claim 1 where the phenol is a monoalkyl phenol.

4. The method of claim 3 where the phenol is a cresol.

5. The method of claim 1 where the olefin is isobutylene.

* * * * *